(12) United States Patent
Olson et al.

(10) Patent No.: US 6,889,727 B2
(45) Date of Patent: May 10, 2005

(54) APPARATUS AND METHOD FOR THE PREPARATION OF EXPERIMENTS USING PROTEINS CONTAINED WITHIN GELS

(75) Inventors: Jeffrey A. Olson, Libertyville, IL (US); Mark L. Chiu, Kenosha, WI (US); Jeffrey Y. Pan, Lake Forest, IL (US); Michael D. McCoy, Lakemoor, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/371,921

(22) Filed: Feb. 21, 2003

(65) Prior Publication Data

US 2004/0163730 A1 Aug. 26, 2004

(51) Int. Cl.$^7$ ............................................. B65B 43/42
(52) U.S. Cl. ......................... 141/130; 141/2; 141/102; 141/284
(58) Field of Search .............................. 141/2, 98, 100, 141/102, 130, 250, 270, 279, 284; 433/90; 222/160, 309, 325–327

(56) References Cited

U.S. PATENT DOCUMENTS

| 3,729,256 | A | * | 4/1973 | Westfall et al. ............... 355/18 |
| 4,651,503 | A | * | 3/1987 | Anderson et al. ............. 53/440 |
| 5,129,825 | A | * | 7/1992 | Discko, Jr. ................... 433/90 |
| 5,454,268 | A | | 10/1995 | Kim |
| 6,402,837 | B1 | | 6/2002 | Shtrahman et al. |

FOREIGN PATENT DOCUMENTS

| EP | 0553539 | 8/1993 |
| WO | 0205962 | 1/2002 |

OTHER PUBLICATIONS

G. Rummel, et al, "Lipidic Cubic Phases: New Matrices for the Three–Dimensional Crystallization of Membrane Proteins", Journal of Structural Biology 121, 82–91 (1998).

Martin Caffrey, "Kinetics and Mechanism of the Lamellar Gel/Lamellar Liquid–Crystal and Lamellar/Inverted Hexagonal Phase Transition in Phosphatidylethanolamine: A Real –Time X–ray Diffraction Study Using Synchrotron Radiation", Biochemistry 24, 4826–4844 (1985).

E.S. Lutton, "Phase Behavior of Aqueous System of Monoglycerides", The Journal of The American Oil Chemists' Society 42, 1068–1070 (1965).

A. Cheng, et al, "A simple mechanical mixer for small viscous lipid–containing samples", Chemistry and Physics of Lipids 95, 11–21 (1998).

E. M. Landau, et al, "Lipidic cubic phases: A novel concept for the crystallization of membrane proteins", Proc. Natl. Acad. Sci. USA 93, 14532–14535 (1996).

Invitation to Pay Additional Fees for International Application No. PCT/US2004/005079.

* cited by examiner

Primary Examiner—Timothy L. Maust
(74) Attorney, Agent, or Firm—David L. Weinstein (57) ABSTRACT

An apparatus and method for dispensing protein-containing materials, such as, for example, pastes, gels, lipidic cubic phases, lipidic mesophases, and mixtures of the foregoing into containers, e.g., wells of assay trays. The invention further provides a method for preparing the aforementioned containers for various experiments involving soluble proteins or membrane proteins or both types of proteins. In a preferred embodiment, the apparatus includes (a) a gel dispenser assembly for dispensing small quantities of gels; (b) a pipette probe for dispensing fluids; (c) an actuator for moving the gel dispenser assembly vertically relative to the pipette probe; (d) a liquid-handling robot having a robot arm for moving the pipette probe and the gel dispenser assembly vertically and horizontally relative to containers, e.g., wells of assay trays; (e) at least one pump for delivering a substantially incompressible fluid to the gel dispenser assembly; and (f) at least one pump for delivering reagents, and, optionally, other materials, to the pipette probe.

17 Claims, 7 Drawing Sheets

APPARATUS AND METHOD FOR THE PREPARATION OF EXPERIMENTS USING PROTEINS CONTAINED WITHIN GELS

BACKGROUND OF THE INVENTION

1. Field of the Invention

This invention relates to an apparatus and method for preparing experiments using proteins that are contained within gels. More particularly, the apparatus and method relates to dispensing minute quantities of protein-containing gels into containers, e.g., assay trays, by means of automated equipment.

2. Discussion of the Art

Membrane proteins, which reside in highly insulating lipid bilayers, catalyze vital reactions, such as solute transport, charge separation, and conversion of energy, as well as signal transduction. In so doing, membrane proteins enable rapid communication between the interior and exterior of living cells. Examples of membrane proteins include ion channels, signaling receptors, hormone receptors, light receptors, and adhesion proteins. Such membrane proteins are the targets of drugs under development to treat numerous ailments. Understanding such processes at a molecular level requires knowledge of the structures of these hydrophobic proteins at high resolution. Structures of proteins are often determined by a study of their crystals, e.g., by x-ray crystallography. Membrane proteins are difficult to crystallize, on account of their hydrophobic and/or lipophilic nature, which makes them difficult to purify in large quantity and reduces their solubility in aqueous solutions. Membrane proteins tend to be unstable at concentrations in aqueous solutions that are required for the nucleation of crystal growth by crystallization methods used for soluble proteins, i.e., those proteins that are not bound to a membrane.

Landau, E. M. and Rosenbusch, J. P. (1996) Proc. Natl Acad. Sci. USA 93, 14532–14535), describe the use of lipidic cubic phases for the crystallization of membrane proteins. According to this method, detergent solubilized membrane protein is mixed with monoolein or monopalmitolein and water or buffered solutions, followed by several centrifugation steps. This method allowed for gentle mixing of the materials over a period of two to three hours to create a viscous, bicontinuous cubic phase, a cured bilipid layer, extending in three dimensions and permeated by aqueous channels. The membrane proteins can partition into the lipid bilayer and can diffuse in three dimensions, thereby allowing them to explore many potential spatial packing configurations that can lead to crystal growth of the protein within lipidic mesophases, e.g., the lipidic cubic phase.

Rummel, G., Hardmeyer, A., Widmer, C., Chiu, M., Nollert, P., Locher, K., Pedruzzi, I., Landau, E. M., & Rosenbusch, J. P. (1998) J. Struct. Biol. 121, 82–91, describe a method for preparing cubic phases by mixing dry lipids with aqueous solutions that contain protein and detergent. The water/lipid ratios are chosen according to the known phase diagrams of the pure/lipid water systems. Cubic phase formation is achieved by centrifugation, and is considered complete once the matrix forms a transparent, nonbirefringent solid material.

Cheng, A., Hummel, B., Qiu, H. & Caffrey, M. (1998) Chem. Phys. Lipids 95, 11–21, describe a simple device for rapid and convenient hydration and mixing of small volumes (10–500 $\mu$l) of viscous hydrated lipid samples for use in X-ray diffraction/scattering and other applications. The device is a low-dead volume (3.6–11.2 $\mu$l) device that was built to facilitate maximal transfer of homogeneously hydrated lipid from the mixer into 1 mm diameter X-ray capillaries with minimal loss of water during transfer and sample manipulation. The device consists of two microsyringes joined by a small-bore coupling needle. The paper also describes a technique for determining the water content of the small volume, hydrated samples prepared with the mixer and an accessory for heating and/or degassing samples during mixing. The mixing is achieved by extruding the lipid through a small orifice. In this method, the likelihood of syringe breakage, upon which all protein is lost, is high.

In an alternative method, the lipid can be melted, mixed with a protein-containing solution by means of a spatula, and undergo centrifugation by means of a tabletop centrifuge for a period of 10 to 15 minutes. The mixing and centrifugation can be repeated several times, typically three times. The sample can then be introduced to a syringe and then dispensed by hand or with a ratcheted dispenser into capillary tubes.

The primary problems associated with dispensing protein-containing lipidic cubic phase from a syringe by hand are the inconsistency of application of the protein-containing phase and the significant manual labor required to prepare a large number of samples. Likewise, the application of precipitating agent is laborious. Furthermore, the capillary tubes had diameters of unreliable size, which decreased reproducibility of experiments. Also, only batch crystallization, in which a small quantity of protein-containing phase is immersed in a precipitating solution, was possible with capillary tubes.

WO 02/05962 A1 describes a method of transferring viscous material, such as lipidic cubic phase material from a first syringe barrel to a second syringe barrel. The transfer can be carried out by providing a first syringe barrel containing a volume of viscous material, the first syringe barrel having a first volume size; providing a coupling device; coupling the first syringe barrel with the coupling device; providing yet another syringe barrel having a different volume size from that of the first syringe barrel; coupling this second syringe barrel with the coupling device; and utilizing air pressure to transfer at least a portion of the viscous material to the second syringe barrel from the first syringe barrel.

U.S. Pat. No. 5,454,268 A describes a device that measures and dispenses accurate and reproducible volumes of normal, viscous, or low-density organic liquid. The device consists of a rigid cylindrical tube containing a main coil spring, which makes the core shaft move, a double-plunger attached on the low end of the core shaft, and a syringe barrel attached securely on the low end of the cylindrical tube. The coil spring is supported by the lower end plug through which the core shaft moves.

It would be desirable to eliminate problems such as imprecise dispensing of lipidic cubic phase in crystallization trays. It would be desirable to reduce the high level of manual labor that is necessary to prepare large numbers of crystallization experiments involving membrane bound proteins. Furthermore, it would be desirable to have an alternate method of dispensing soluble proteins or membrane proteins in other silica gels, agarose gels, sol/gels, and hydrogels that are commonly used in crystallization processes.

SUMMARY OF THE INVENTION

The invention provides an apparatus and method for dispensing protein-containing materials, such as gels, pastes, lipidic cubic phases, lipidic mesophases, and mixtures of the foregoing (hereinafter alternatively referred to as gels) into containers, e.g., wells of assay trays or crystallization trays. The invention further provides a method for preparing the aforementioned trays for various experiments involving soluble proteins or membrane proteins or both types of proteins.

In one aspect, this invention provides an apparatus comprising:

(a) a gel dispenser assembly for dispensing small quantities of gels;
(b) a pipette probe for dispensing fluids;
(c) an actuator for moving the gel dispenser assembly vertically relative to the pipette probe;
(d) a liquid-handling robot having a robot arm for moving the pipette probe and the gel dispenser assembly vertically and horizontally relative to containers, e.g., wells of assay trays;
(e) at least one pump capable of delivering liquids to the pipette probe or to the gel dispenser assembly or to both the pipette probe and the gel dispenser assembly.

In the preferred embodiments, the apparatus comprises at least a second pump, so that one of the two pumps delivers liquid material to the pipette probe and the other of the two pumps delivers liquid material to the gel dispenser assembly. In the preferred embodiments, liquid materials to be delivered to the pipette probe include reagents and other liquid materials, e.g., wash fluid, and the liquid material to be delivered to the gel dispenser assembly includes a substantially incompressible fluid, e.g., water or mineral oil. In an alternative embodiment, a single pump can be employed to deliver reagents and other liquid materials, e.g., wash fluid, to the pipette probe and a substantially incompressible fluid to the gel dispenser assembly.

The gel dispenser assembly comprises (1) a gel-dispensing barrel having a bore, (2) a drive barrel having a bore, (3) a dual-head piston, and (4) a gel-dispensing nozzle. The dual-head piston comprises (a) a first head, i.e., the drive piston, which fits within the bore of the drive barrel, and (b) a second head, i.e., the driven piston, which fits within the bore of the gel-dispensing barrel. In the preferred embodiments, the surface area of the first head is larger than the surface area of the second head. The dual-head piston acts as a pressure intensifier. A substantially incompressible fluid, i.e., drive fluid, delivered at relatively low pressure by a pump to the gel dispenser assembly pushes against the drive piston. This force is directly transmitted to the driven piston, which then produces an intensified pressure in the gel, which has been loaded into the gel-dispensing barrel such that there are substantially no air pockets or voids between the driven piston and the gel-dispensing nozzle. The ratio of the pressures experienced by the two heads of the dual-head piston is inversely proportional to the ratio of the surface areas of the two heads of the dual-head piston, e.g., if the surface area of the drive piston is equal to five times that of the driven piston, the pressure in the gel will be approximately five times the pressure acting on the drive piston. In an alternative embodiment, the surface area of the drive piston is equal to or smaller than the surface area of the driven piston. In this alternative embodiment, the dual-head piston acts as a pressure reducer.

In another aspect, this invention provides a method for dispensing a gel into a container, e.g., the well of an assay tray. In a preferred embodiment, the fundamental principle involves:

(1) the preparation of the gel and loading thereof into a gel dispenser assembly chamber that can be equipped with a gel-dispensing nozzle;
(2) positive displacement dispensing of the protein-containing gel into a plurality of containers, e.g., wells of an assay tray;
(3) preparation of the containers, e.g., the wells of an assay tray, for various experiments by automated addition of precipitating buffers or other reagents. Optionally, humidity can be controlled to reduce changes in concentration of the reagents due to evaporation while assay trays are being prepared.

In a preferred embodiment, the method comprises the steps of:

(a) providing an apparatus comprising (1) a gel dispenser assembly for dispensing small quantities of gels, the gel dispenser assembly comprising (i) a gel-dispensing barrel having a bore, (ii) a drive barrel having a bore, (iii) a dual-head piston, and (iv) a gel-dispensing nozzle; (2) a pipette probe for dispensing fluids; (2) an actuator, preferably a pneumatic cylinder actuator, for moving the gel dispenser assembly vertically relative to the pipette probe; (3) a liquid-handling robot having a robot arm for moving the pipette probe and the gel dispenser assembly vertically and horizontally relative to containers, e.g., wells of assay trays; (4) a first pump, preferably a syringe pump, for delivering a substantially incompressible fluid to the gel dispenser assembly; and (5) a second pump, preferably a syringe pump, for delivering liquids, e.g., reagents, wash fluid, and, optionally, other liquid materials, to the pipette probe;

(b) introducing gel into the gel-dispensing barrel;

(c) advancing, by means of pressure provided by the substantially incompressible fluid, the driven piston inside the gel dispenser assembly until gel begins to flow from the gel-dispensing nozzle;

(d) dispensing a small quantity of gel into a container; and (e) dispensing a metered quantity of a reagent, e.g., precipitating agent, into the container by means of the second pump.

It is also preferred that the drive piston of the gel dispenser assembly be primed with the substantially incompressible fluid by means of the first pump prior to step (c). In an alternative embodiment, a single pump can be employed to deliver reagents and other liquid materials, e.g., wash fluid, to the pipette probe and a substantially incompressible fluid to the gel dispenser assembly.

The apparatus and method of this invention can be used to crystallize proteins, either soluble proteins or membrane proteins, by means of any one of numerous methods, such as, for example, a free interface diffusion method, a sitting drop method, or a batch method. The invention can also be used to characterize ligand binding of proteins within the lipidic cubic phase, the agarose phase, or other viscous phase.

BRIEF DESCRIPTION OF THE DRAWINGS

FIG. 3B also shows the pipette probe positioned above the well of the assay tray filled by the gel dispenser assembly in FIG. 3A.

DETAILED DESCRIPTION

As used herein, the expression "protein structure" means a protein structure suitable for use in the field of structure-based drug design. Typically, a protein structure intended for use in this invention is a high-resolution protein structure having an atomic resolution no higher than 2.7 Angstroms. The expression "membrane protein structure" means a protein that is associated with the membrane bilayer of cells. In many cases, a membrane protein is not soluble in an aqueous solution in the absence of detergents or lipids. The expression "soluble protein structure" means a protein that is soluble in an aqueous solution. The expression "lipidic cubic phase" means a lipid phase that has a cubic symmetry. See Rummel, G., Hardmeyer, A., Widmer, C., Chiu, M., Nollert, P., Locher, K., Pedruzzi, I., Landau, E. M., & Rosenbusch, J. P. (1998) J. Struct. Biol. 121, 82–91, incorporated herein by reference. The expression "protein-containing cubic lipid phase" means a lipidic cubic phase that contains protein within the phase. The expression "lipidic mesophase" means a mixture of phases of lipids that contains (a) the components needed to make the lipidic cubic phase coexist with (b) the lipidic lamellar phase or (c) the lipidic hexagonal phase or (d) both the lipidic lamellar phase and the lipidic hexagonal phase.

The expression "free interface diffusion method" means a method of crystallization in which a solution containing a protein is placed adjacent to a solution of precipitating agent in a tube. At the interface between the two solutions, mixing occurs, which may bring about crystallization of the protein. The expression "sitting drop method" means a method of crystallization in which a solution containing a protein is placed above a reservoir containing a solution of precipitating agent. When the system is placed in an environment sealed from the ambient environment, the solution of protein is concentrated on account of diffusion of vapor, thereby possibly resulting in crystallization of the protein. The expression "batch method" means a method of crystallization in which there is a direct mixing of a solution of protein with a solution of precipitating agent. The latter solution alters the solubility of the protein or the electrolytic properties of the former solution to bring about crystallization of the protein.

The expression "positive displacement" means a characteristic of certain types of pumps in which the volumetric output from the pump is relatively independent of back-pressure. Back-pressure is the pressure of the fluid downstream of the pump, i.e., the pressure that the pump must overcome to deliver fluid. The expression "surface area" means the area of the surface of the head of a piston that comes into contact with a fluid. By employing conventional seals, the fluid used to drive the drive piston will contact only the top surface of the drive piston. The expression "remotely-powered" means that the source of power is detached from the object to which power is being delivered. The expression "target surface" means the surface onto which a gel is to be deposited, such as, for example, the bottom of a well of an assay tray. The term "gel" includes, but is not limited to, protein-containing materials, such as gels, pastes, lipidic cubic phases, lipidic mesophases, and mixtures of the foregoing. The expression "pressure intensification", and the like, means an increase or amplification of the pressure in a fluid. The expression "pressure reduction", and the like, means a decrease of the pressure in a fluid. The terms "primed", "priming", and the like mean the process of filling the interior volume of a drive fluid chamber with drive fluid. The expression "liquid-handling robot" means any multi-functional, programmable device used to handle liquids. The expression "pipette probe" means a tube, open at both ends, that is used to transfer small volumes of liquid.

Figure 1:
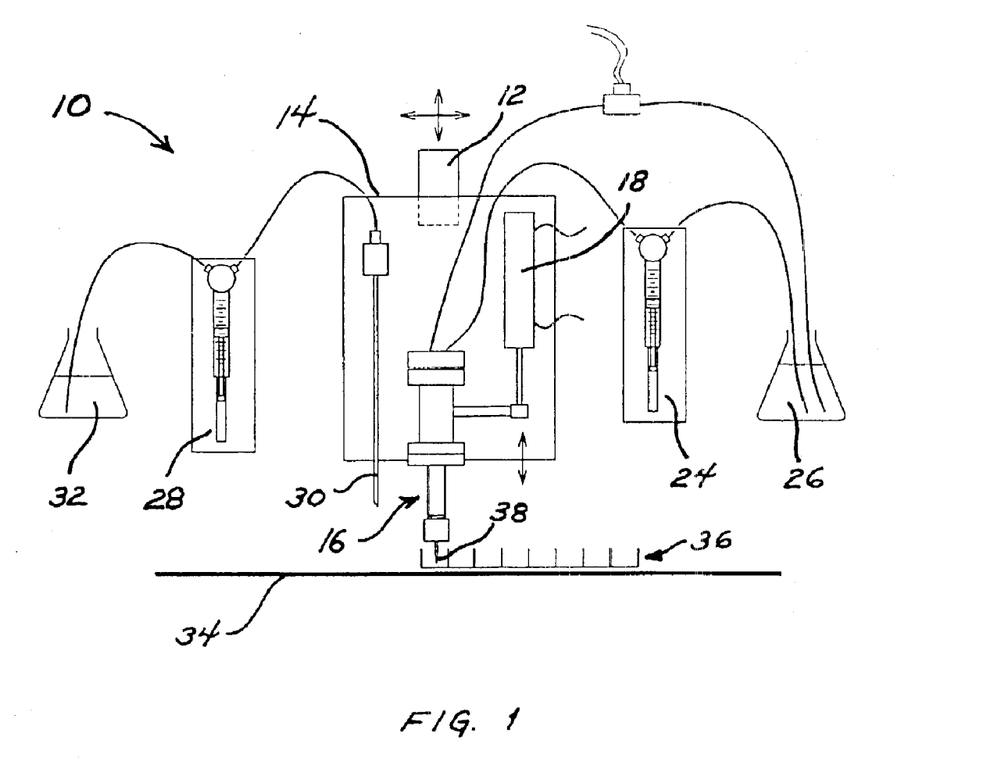
FIG. 1 is a schematic diagram of a preferred embodiment of the system of this invention.

Referring now to FIG. 1, the apparatus 10 comprises a liquid-handling robot that includes a robot arm assembly 12. The liquid-handling robot is capable of moving the robot arm assembly 12 in three directions—X, Y, and Z. A representative example of such a liquid-handling robot having a robot arm assembly 12, which liquid-handling robot is commercially available, is the Gilson 215 Liquid Handler (Gilson, Inc., Middleton, Wis.). A mount plate 14 is attached to the robot arm assembly 12 of the liquid-handling robot, so that the motion of the mount plate 14 is substantially identical to that of the robot arm assembly 12. In a preferred embodiment, the mount plate 14 is attached to the robot arm assembly 12 with screws, bolts, or some other type of mechanical fastener. The materials and dimensions of the mount plate 14 are not critical, but in one embodiment, the mount plate is made of an aluminum sheet having the approximate dimensions of 10 inches by 3 inches by ⅛ inch. A gel dispenser assembly 16, preferably remotely powered, and an actuator 18, preferably a pneumatic cylinder actuator, are attached to the mount plate 14 so that these components move simultaneously with the X, Y, and Z translations of the robot arm assembly 12. A representative example of a commercially available actuator 18 is the "Bimba Original Line Cylinder", bore size of 5/16-inch (8 mm), available from Bimba Manufacturing Company, Monee, Ill. The length of the actuator 18 is not critical, but in one embodiment, the length of the actuator is approximately 5 inches. The actuator 18 enables the gel dispenser assembly 16 to be extended vertically and retracted vertically, as needed, in relation to the robot arm assembly 12. In a preferred embodiment, a pump 24, preferably a syringe pump, positioned remotely from the gel dispenser assembly 16, delivers substantially incompressible fluid to the gel dispenser assembly 16. The pump 24 does not have to be remotely positioned, but, because pumps are typically bulky and heavy, it is preferred that the pump 24 be positioned remotely so that it does not have to move in conjunction with the robot arm assembly 12. The substantially incompressible fluid, such as water, hydraulic oil, mineral oil, and the like, applies pressure to the drive piston component of the gel dispenser assembly. Gases and other compressible fluids, such as nitrogen or air, are not desirable. The substantially incompressible fluid is stored in a reservoir 26. In another embodiment, pressure can be applied to the drive piston component of the gel dispenser assembly 16 by means of a drive mechanism, preferably a direct drive mechanism, such as, for example, by a motor or screw positioned directly over the gel dispenser assembly 16. In this type of embodiment, the gel dispenser assembly 16 would not be remotely driven.

Wash fluid and other reagents can be dispensed by means of a conventional pump 28, preferably a syringe pump, connected to a pipette probe 30 extending from the robot arm assembly 12. The pump 28 is typically included with a conventional liquid-handling robot, such as the liquid-handling robot mentioned previously. The pipette probe 30, which extends from the robot arm assembly 12, can be washed periodically by means of a bath that is supplied with fluid from a wash fluid reservoir 32. The apparatus 10 further comprises a deck 34, upon which one or more assay trays 36 are positioned, so that they are accessible to both the pipette probe 30 and a gel-dispensing nozzle 38, when the gel-dispensing nozzle 38 is in its extended position. The external diameter of the gel-dispensing nozzle 38 must be small enough, e.g., 1 mm outside diameter, so that it can be inserted into the wells of the assay tray 36. The gel-dispensing nozzle 38 is preferably of sufficient length to reach the bottom surfaces of the wells of the assay tray 36. The liquid-handling robot can be utilized to dispense both gels and reagents into any type of assay tray 36 desired.

Figure 2:
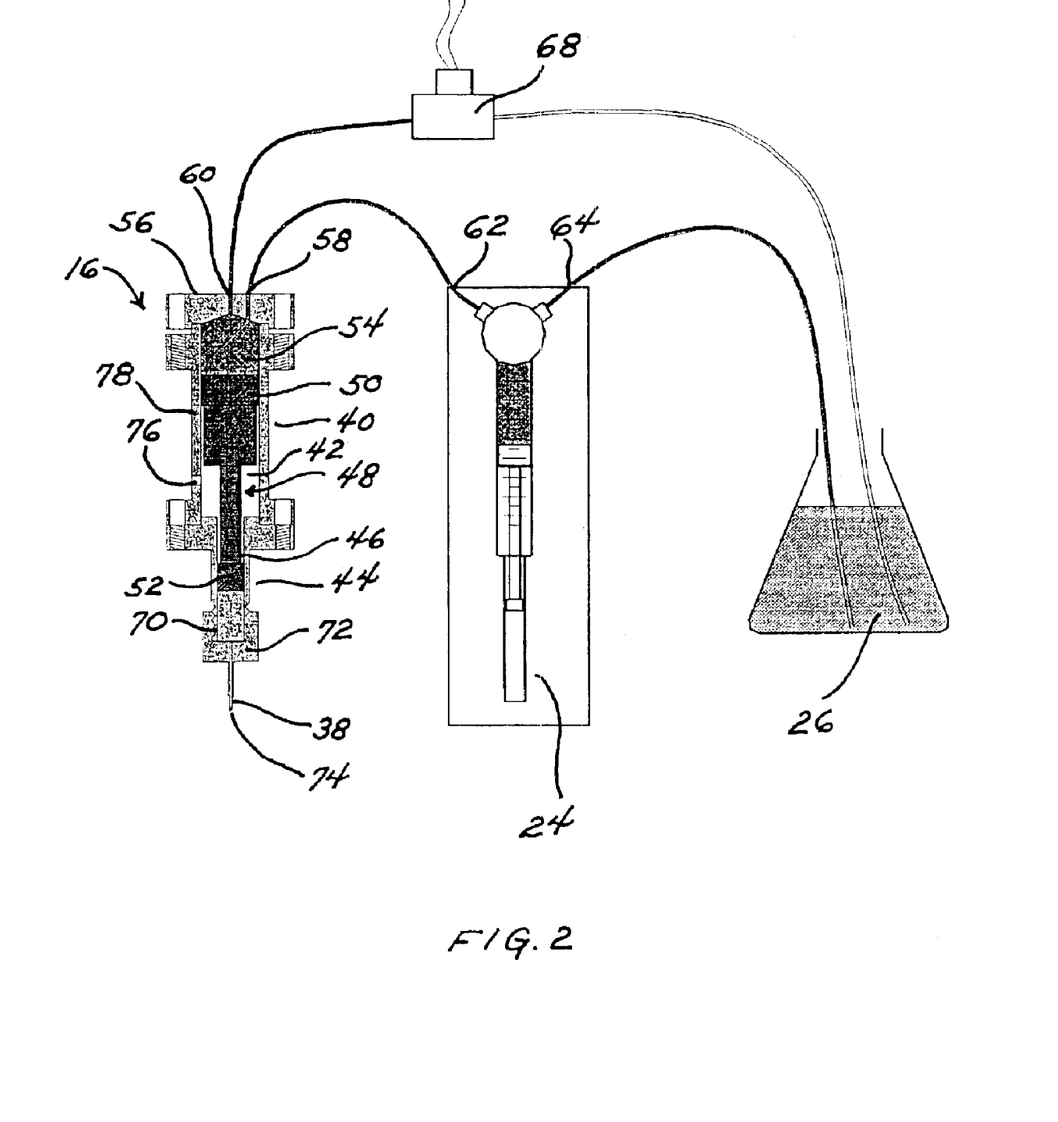
FIG. 2 is a schematic diagram showing a side view in elevation of a cross section of the gel dispenser assembly of the system of this invention.

Referring now to FIG. 2, which depicts the preferred embodiment, the gel dispenser assembly 16 comprises a drive barrel 40 having a relatively large bore 42, e.g., 14.5 mm in diameter, the drive barrel 40 being attached to a gel-dispensing barrel 44 having a relatively small bore 46, e.g., 6.5 mm in diameter. The dimensions of the gel dispenser assembly 16 are not critical, but in one embodiment, the overall length of the gel dispenser assembly is approximately 4 inches, with the drive barrel 40 having a length of approximately 2 inches and the gel-dispensing barrel 44 having a length of approximately 1¼ inch. A dual-head piston 48 is installed within the bores 42 and 46 of the barrels 40 and 44, respectively, such that the large head 50 of the dual-head piston 48, i.e., the drive piston, fits precisely within the bore 42 of the drive barrel 40, and the small head 52 of the dual-head piston 48, i.e., the driven piston, fits within the bore 46 of the gel-dispensing barrel 44. The ratio of the surface area of the large head 50 of the dual-head piston 48 to the surface area of the small head 52 of the dual-head piston 48 preferably ranges from greater than about 1:1 up to about 1000:1, more preferably up to about 100:1, even more preferably up to about 10:1. In an alternative embodiment, not shown, the gel dispenser assembly can comprise a drive barrel having a relatively small bore, the drive barrel being attached to a gel-dispensing barrel having a relatively large bore. In this alternative embodiment, the dual-head piston is installed within the bores of the barrels such that the small head of the dual-head piston fits precisely within the bore of the drive barrel, and the large head of the dual-head piston fits within the bore of the gel-dispensing barrel. In this alternative embodiment, the ratio of the surface area of the small head of the dual-head piston to the surface area of the large head of the dual-head piston preferably ranges from about 1:1 to less than about 1:1, e.g., to about 1:10.

Returning now to the description of the preferred embodiment, as shown in FIG. 2, a drive fluid chamber 54 of the drive barrel 40 is sealed by a vented cover 56, which has two ports—a drive fluid inlet port 58 and an outlet port 60, which functions as a vent. The ports have internal diameters of approximately 1 mm. The pressure inlet port 58 communicates with the outlet port 62 of the pump 24. It is preferred that the pump 24 be motor-driven. A representative example of a commercially available motor-driven pump 24 is Cavro XL, available from Cavro Scientific Instruments, Sunnyvale, Calif. The inlet port 64 of the pump 24 is connected to the reservoir 26, which contains water or some other substantially incompressible fluid, as desired. The water or substantially incompressible fluid pushes on the drive piston 50, which in turn pushes on the driven piston 52 in order to force gel out of the gel dispenser assembly 16. The vent 60 in the vented cover 56 is connected by means of a shut-off valve 68, preferably a solenoid shut-off valve, to the reservoir 26. A representative example of a commercially available shut-off valve 68 is the NResearch 2-way isolation valve, 1.5 mm orifice, available from NResearch, Inc., West Caldwell, N.J.

A removable gel-dispensing nozzle 38 is attached to and sealed to one end 70 of the gel-dispensing barrel 44 by means of an adapter 72. As shown in FIG. 2, the adapter 72 is attached to the end 70 of the gel-dispensing barrel 44 by screw threads. Other means of attachment can also be used, e.g., friction fitting, snap fitting, etc. The tip 74 of the gel-dispensing nozzle 38 preferably comprises a stainless steel micro-tube having a small diameter, e.g., 0.02 inch (0.5 mm) inside diameter. A vent 76 (e.g., 1.5 mm in diameter) in the side-wall 78 of the drive barrel 40 prevents the build-up of pressure in the air space between the piston heads 50 and 52 of the dual-head piston 48.

Figure 3A:
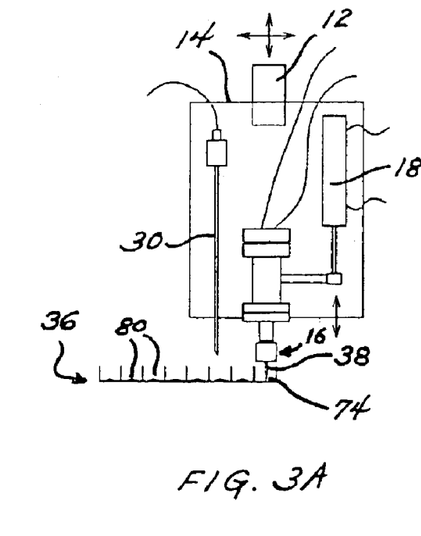
FIG. 3A is a schematic diagram showing the gel dispenser assembly of the system of this invention extending into a well of an assay tray.
Figure 3B:
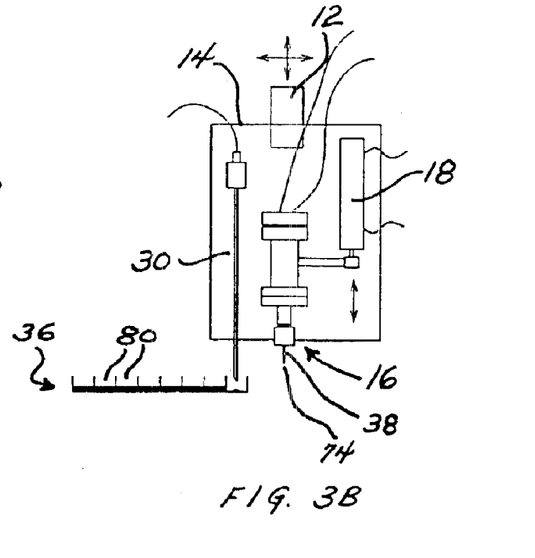
FIG. 3B is a schematic diagram showing the gel dispenser assembly of the system of this invention retracted from the well of the assay tray shown in FIG. 3A.

FIGS. 3A, 3B, 3C, 3D, and 3E illustrate how the system of this invention can be utilized to set up a large number of protein crystallization experiments or ligand binding experiments. Referring to FIG. 3A, the gel dispenser assembly 16 is used to dispense tiny, measured beads of gel to the bottom of each well 80 in an appropriate assay tray 36. The movements of the gel dispenser assembly 16 are precisely controlled by standard move commands performed by the liquid-handling robot. After the beads of gel have been dispensed, the gel dispenser assembly 16 is retracted and the pipette probe 30 is used to deliver precise volumes of precipitating buffer or other reagents into each well 80 of the assay tray 36. See FIG. 3B. After the wells 80 have been prepared, the assay tray 36 is covered and removed from the instrument 10 for incubation.

Figure 3C:
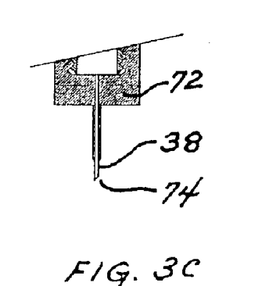
FIG. 3C is a schematic diagram showing an enlarged view of the tip of the gel dispenser assembly shown in FIGS. 3A and 3B.
Figure 3D:
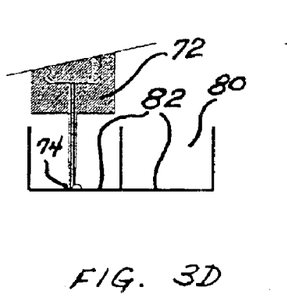
FIG. 3D is a schematic diagram showing an enlarged view of the tip of the gel dispenser assembly shown in FIG. 3A extended into a well of the assay tray shown in FIG. 3A.
Figure 3E:
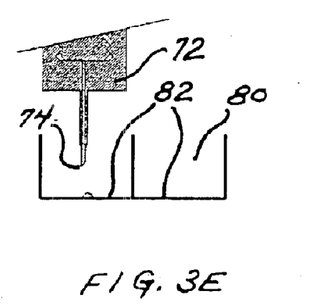
FIG. 3E is a schematic diagram showing an enlarged view of the tip of the gel dispenser assembly shown in FIG. 3A partially retracted from the well of the assay tray shown in FIG. 3A.

In order to accurately and precisely dispense tiny beads of gel (typically from a volume of about 1.0 $\mu$L or higher down to a volume of about 0.2 $\mu$L or even lower), it is essential that the dimensions of the tip 74 of the gel-dispensing nozzle 38 be very small, e.g., 0.001 inch to 0.050 inch (0.025 mm to 1.25 mm). FIG. 3C shows the design details of one gel-dispensing nozzle, which has been found to be useful in this invention. Once the gel bead has emerged from the gel-dispensing nozzle 38, release of the gel bead can be difficult, because the gel is sticky and tends to cling to the tip 74 of the gel-dispensing nozzle 38. This problem can be addressed in a variety of ways. In one embodiment, the tip 74 of the gel-dispensing nozzle 38 can be designed so that when the tip 74 is in contact with a target surface, e.g., the bottom of a well of an assay tray, at least a portion of the gel within the tip 74 is not completely sealed within the tip 74 by said target surface. Such a design can be accomplished by employing a beveled tip, a notched tip, or a scalloped tip. In a preferred embodiment, the tip 74 is beveled, preferably at an angle of approximately 45° to the major axis of the tip 74, as shown in FIG. 3C. To release the gel, the tip 74 is brought very close to or into contact with a target surface 82 before the gel is dispensed. Because of the bevel configuration, the gel can escape from the tip 74 even though the tip 74 is touching the target surface. After the gel is dispensed, the tip 74 can be retracted vertically, thereby leaving the gel bead attached to the target surface 82. See the figures FIG. 3D and FIG. 3E. An alternate method involves the steps of dispensing the desired bead of gel with the tip 74 of the gel-dispensing nozzle 38 in a position raised above the target surface 82. Next, the tip 74 is lowered until it contacts the target surface 82; then, the tip 74 is moved laterally a small distance relative to the target surface 82 in order to "wipe" the gel from the tip 74. Both methods have been used successfully.

Figure 4:
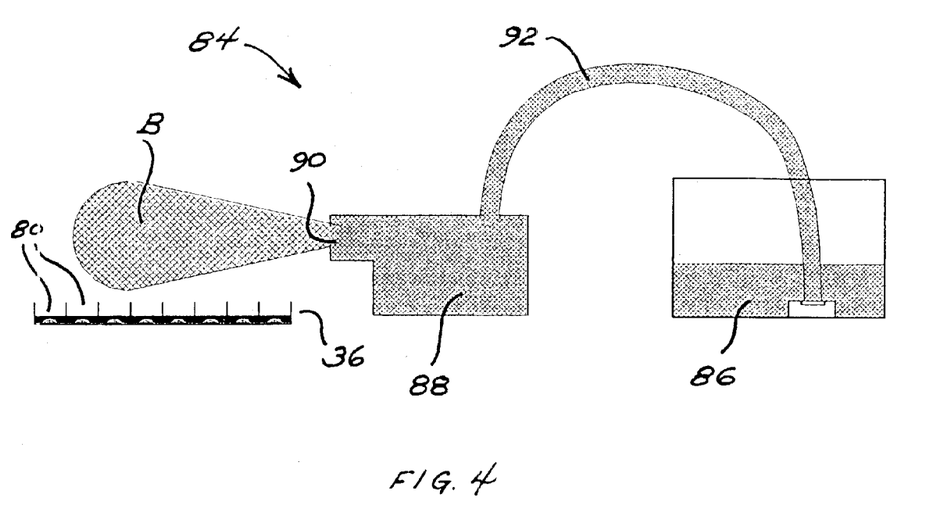
FIG. 4 is a schematic diagram showing how an atomizer can be set up to provide a humid environment over an assay tray.

In some assays the volumes of solvent-borne reagents dispensed is very small, with the result that evaporation of solvent could significantly alter the concentrations of components within the reagents. To reduce the effects of evaporation of solvent, an evaporation control system 84, as shown in FIG. 4, can be used. Because reagents are, in most cases, carried by water, an aqueous system will be described. However, the same principles for aqueous systems operate in the cases where the solvent is one other than water. An adjustable atomizer 86, preferably an ultrasonic atomizer, delivers water mist to a distribution manifold 88 placed in proximity to the assay trays 36. The distribution manifold 88 has an outlet nozzle 90 for directing the mist toward the assay trays 36. The dimensions and height of the outlet nozzle 90 are selected to be compatible with the geometry of the assay tray 36. In addition, a delivery tube 92 transfers the mist from the atomizer 86 to the distribution manifold 88. The function of the humidity control system 84 is to envelop the assay trays 36 with a blanket of locally humid air, designated by the letter "B". As used herein, the term "locally" means in the vicinity of the assay trays 36. Preferably, the humidity of air in contact with the assay trays 36 is at 100% R.H. or as near to this level as possible. By using an ultrasonic atomizer 86 rather than a heated-water generator, the temperature of the mist stream can be made very close to ambient, and, consequently, any tendency to condense water onto the assay trays 36 is minimized.

The gel dispenser assembly 16 preferably involves the principle of pressure intensification to dispense precise quantities of the gel. In an alternative embodiment, which is less preferred, the gel dispenser assembly involves the principle of pressure reduction to dispense precise quantities of the gel. The techniques developed for filling the gel dispenser assembly 16 minimize the possibility of air bubbles being present in the gel. The use of a dual-head piston 48 driven by a positive-displacement pump 24 allows for precise dispensing of the protein-containing gel down to a volume of 0.2 μL or even lower, if necessary. Precise dispensing of smaller volumes of protein-containing gel permits broader sampling and more diverse examination of crystallization conditions for a given quantity of protein. By placing the gel onto 96-well or 384-well assay trays, the possibility of setting up sitting drop, batch, or free interface diffusion crystallization methods is expanded, thereby increasing the repertoire of protein crystallization experiments using the lipidic cubic phases and other gels. Assay trays also improve the visualization of experimental results and allow the establishment of many more experiments, which can then be stored in a compact manner.

Diverse sets of crystallization conditions can be generated by varying sequential applications of gel, buffer, and precipitating agent. For example, solutions of precipitating agents can be overlaid onto the dispensed gel using the free interface method or the batch method or the sitting drop method. Protein crystals can then be detected via microscopy and analyzed to determine x-ray scattering properties. In the case of ligand binding experiments, solutions of ligands could be applied to the dispensed gel. Detection of bound ligand could be based on presence of ligand markers found in the gel. Competition of bound ligands with other ligands in solution would determine relative specificity of the receptor in the gel.

Through the use of this invention, any commercially available liquid-handling robot can be rendered capable of preparing assay trays for a wide variety of experiments involving protein-containing pastes, gels, lipidic cubic phases, lipidic mesophases, and combinations of the foregoing.

Operation

In a preferred embodiment, the method of this invention can be performed as follows:

1) The gel-dispensing barrel 44 is removed from the gel dispenser assembly 16, filled with gel, and then reattached to the gel dispenser assembly 16. The gel is loaded such that no air pockets or bubbles are present in the gel after it has been loaded into the gel-dispensing barrel 44.

2) The drive piston 50 of the gel dispenser assembly 16 is primed with hydraulic fluid by opening the shut-off valve 68 and pumping large volumes of hydraulic fluid through the drive fluid chamber 54 of the drive barrel 40 until all air has been removed and the drive fluid chamber 54 of the drive barrel 40 is completely filled with fluid.

3) The shut-off valve 68 is closed.

4) The pump 24 is advanced until gel begins to flow from the tip 74 of the gel-dispensing nozzle 38. The gel dispenser assembly 16 is now primed and ready for use.

5) Any further delivery of fluid from the pump 24 results in a predictable amount of gel discharged from the gel-dispensing nozzle 38, e.g., 5 μL of fluid delivered by the pump 24 equates to 1 μL of gel discharged (assuming that the surface area of the head of the large piston 50 of the dual-head piston 48 is 5 times as great as the surface area of the head of the small piston 52 of the dual-head piston 48).

Figure 5A:
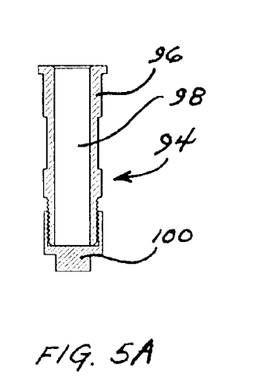
FIG. 5A is a side view in elevation of a cross section of a gel mixing centrifuge tube suitable for preparing a gel.
Figure 5B:
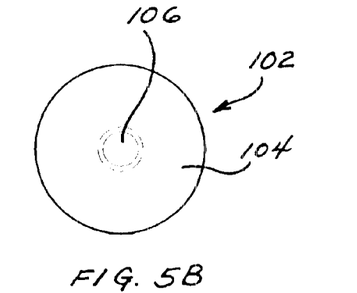
FIG. 5B is a top plan view of an adapter for the gel mixing centrifuge tube of FIG. 5A.
Figure 5C:
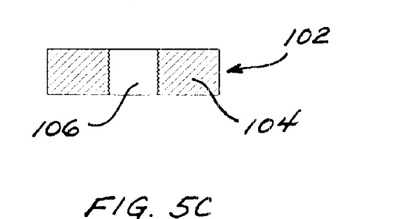
FIG. 5C is a side view in elevation of a cross section of the adapter shown in FIG. 5B.
Figure 5D:
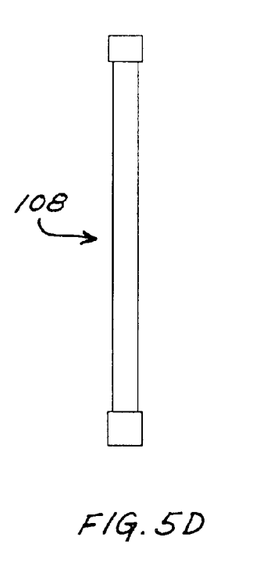
FIG. 5D is a side view in elevation of a push rod that is suitable for transferring a gel from a gel mixing centrifuge tube to a gel dispenser assembly.

In order for the gel dispenser assembly 18 to perform optimally, it is preferred that air pockets or bubbles not be present when the gel is loaded into the gel-dispensing barrel 44. In some situations, the gel dispenser assembly 16 is inherently self-purging, i.e., the undesired air pockets or bubbles are spontaneously cleared from the gel-dispensing barrel 44 during the first few distributions of gel therefrom. However, in order to ensure elimination of air pockets or bubbles, and to provide a simple method for preparing the gels for dispensing, unique gel-handling tools have been developed. FIG. 5A shows a centrifuge tube 94 for mixing gels that has been developed to fit within the rotor pockets of a fixed angle bench-top centrifuge. The centrifuge tube 94 comprises a barrel 96 having a bore 98 and a removable cap 100. The cap can be removably attached to the barrel 96 by means of threads, friction fit, or other mode of removable attachment. FIGS. 5B and 5C show an adapter tool 102, which comprises a cylindrical element 104 having a bore 106. FIG. 5C shows a push rod tool 108, which comprises an elongated cylindrical rod. The gel is prepared by mixing the non-proteinaceous components of the gel with a solution containing a protein through the use of standard procedures. The mixing is carried out by repeatedly agitating the mixture within the centrifuge tube 94, typically with a spatula, followed by centrifugation of the mixture in a bench-top centrifuge for about 15 minutes. Through the use of this technique, any desired quantities of gel can be formed within the centrifuge tube 94.

Figures 6A, 6B:
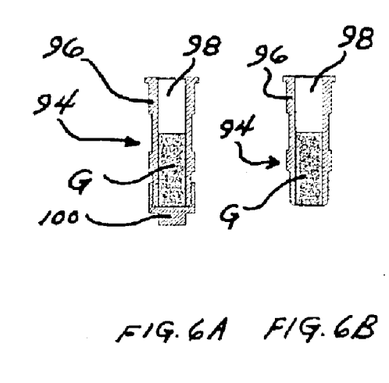
FIGS. 6A, 6B, 6C, 6D, 6E, and 6F are schematic diagrams showing the sequence of steps required for introducing a gel into the gel-dispensing barrel in a preferred embodiment of the invention.
Figure 6C:
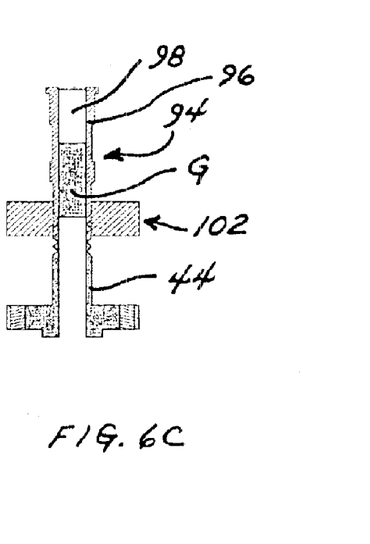
Figure 6D:
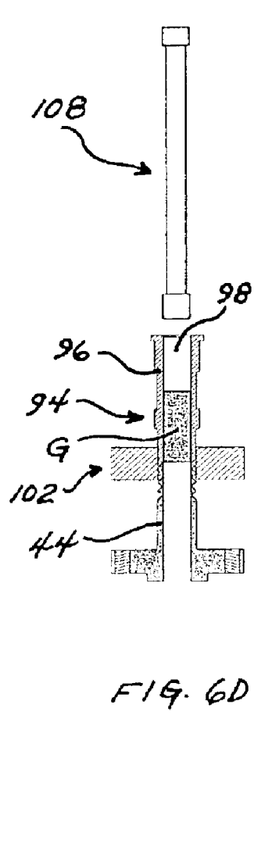
Figure 6E:
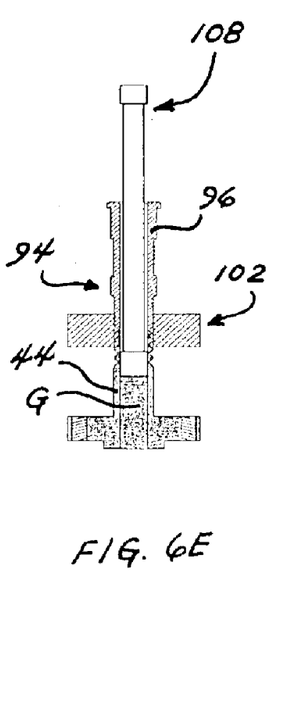
Figure 6F:
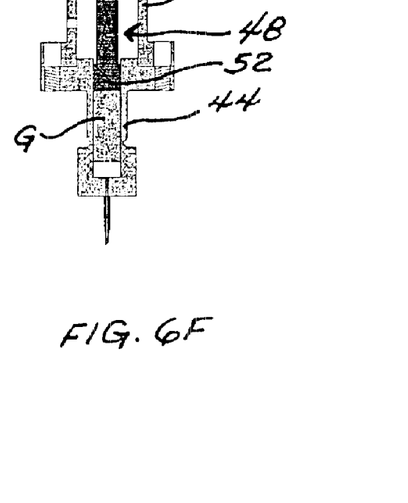

After the gel is formed, it can be introduced into the gel dispenser assembly 16 by the following procedure, which is illustrated in FIGS. 6A, 6B, 6C, 6D, 6E, and 6F. FIG. 6A shows the gel in the centrifuge tube 94 after the gel has been formed. The gel is represented by the letter "G". FIG. 6B shows that the cap 100 has been removed from the barrel 96 of the centrifuge tube 94. The presence of bubbles can be detected by the naked eye after the cap 100 has been removed from the centrifuge tube 94. If any bubbles are detected, they can be removed by centrifugation. FIG. 6C shows an adapter tool 102 that can be used to connect the centrifuge tube 94 with the end 70 of the gel-dispensing barrel 44, which is shown with the gel-dispensing nozzle 38 removed. As stated previously, the gel-dispensing barrel 44 is removed from the gel dispenser assembly 16 and filled with gel before it is reattached to the gel dispenser assembly 16. FIG. 6D and FIG. 6E show the gel being transferred into the gel-dispensing barrel 44 by means of the pushrod tool 108. The use of the pushrod tool 108 is designed to ensure that the gel-dispensing barrel 44 is properly filled, that is, the gel contains no air pockets or bubbles. FIG. 6F shows the gel-dispensing barrel 44, which has been filled with gel, reattached to the gel dispenser assembly 16, and the gel-dispensing nozzle 38 installed. The apparatus 10 can now be used to dispense gel.

Figure 7:
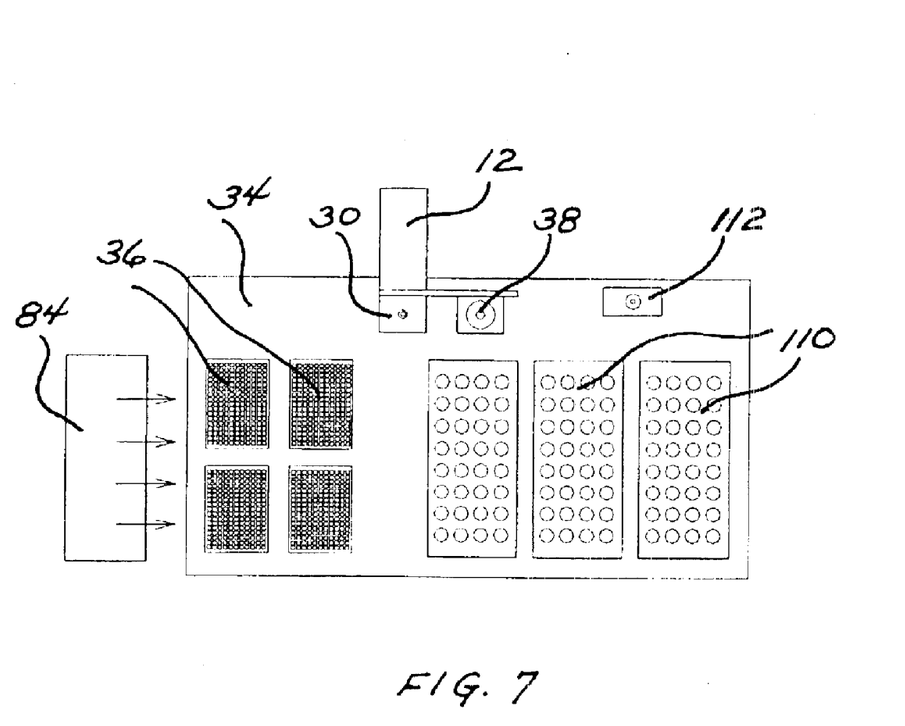
FIG. 7 is a top plan view of the deck of the apparatus of a preferred embodiment of this invention.

FIG. 7 illustrates an embodiment of the deck 34 of the apparatus 10 of this invention. FIG. 7 shows relative positions of the robot arm assembly 12, the assay trays 36, the evaporation control system 84, and trays for reagents and other materials 110. FIG. 7 also shows a position of the pipette probe 30 relative to the gel-dispensing nozzle 38. FIG. 7 further shows a satisfactory location for placing a wash station 112 for rinsing the pipette probe 30.

The present invention provides several advantages, including, but not limited to the following:

1) The power source for the gel dispenser assembly 16 can be located at a remote location. Because only the gel dispenser assembly 16, but not the power source, needs to be mounted onto the mount plate 14, the weight and size of the power source is unimportant. A relatively bulky, heavy commercially available pump can be used.

2) By intensifying the pressure, the pressures experienced by the pump 24 can be maintained as low as desired. Many otherwise attractive pumps are rated to only relatively low pressures, e.g., 100 psi or lower. The pressure required to efficiently dispense the gels, which are very viscous, can be 250 psi or higher. In the absence of pressure intensification, the pressures experienced by the pump 24 might exceed the capability of the pump.

3) The dual-head piston design acts as a pressure intensifier. Drive fluid delivered at relatively low pressure by the pump 24 pushes on the drive piston 50. This force is directly transmitted to the driven piston 52, which then produces an intensified pressure in the gel. The ratio of the pressures is equal to the ratio of the surface areas of the pistons, e.g., if the drive piston 50 has an surface area equal to five times that of the driven piston 52, the pressure in the gel will be approximately five times the pressure acting on the drive piston 50.

4) The use of a dual-head piston also results in a volumetric displacement ratio, e.g., if the ratio of the surface area of the drive piston 50 to the surface area of the driven piston 52 is 5:1, in order to dispense 1 $\mu$L of gel, 5 $\mu$L of substantially incompressible fluid is required. Because the percentage volumetric accuracy of a pump increases with increasing volumes of fluid delivered, the use of a dual-head piston facilitates the accurate and precise dispensing of very small volumes of gel.

5) The substantially incompressible fluid is completely isolated from the valuable protein-containing gel. Any potential to contaminate the gel is eliminated.

6) The gel-dispensing barrel 44 can be easily detached from the rest the gel dispenser assembly 16 for convenient loading of gel.

7) The vent 76 in the wall 78 of the drive barrel 40 provides a visual indication of when the dual-head piston 48 is near its end of travel.

While it is preferred to employ pressure intensification to dispense the gel into a container, it is also acceptable to employ pressure reduction to dispense the gel into a container.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus for dispensing a gel into a container, said apparatus comprising:
   (a) a gel dispenser assembly comprising
      (1) a gel-dispensing barrel having a bore;
      (2) a drive barrel having a bore;
      (3) a dual-head piston; and
      (4) a gel-dispensing nozzle; and
   (b) a pump positioned remotely from said gel dispenser assembly for delivering substantially incompressible fluid to said gel dispenser assembly.

2. The apparatus of claim 1, wherein said dual-head piston comprises (a) a drive piston that fits within said bore of said drive barrel, and (b) a driven piston that fits within said bore of said gel-dispensing barrel.

3. The apparatus of claim 2, wherein the ratio of the surface area of said drive piston to the surface area of said driven piston is greater than about 1:1.

4. The apparatus of claim 2, wherein the ratio of the surface area of said drive piston to the surface area of said driven piston is equal to or less than about 1:1.

5. The apparatus of claim 2, wherein said drive piston transmits pressure to said driven piston.

6. The apparatus of claim 1, wherein said gel-dispensing barrel is capable of being detached from said apparatus.

7. The apparatus of claim 1, further including an opening in said drive barrel to vent a chamber between said drive piston and said driven piston.

8. The apparatus of claim 1, wherein said apparatus is coupled to a programmable positioning device, whereby said apparatus is capable of being moved to a plurality of positions.

9. A method for dispensing a gel into a container, said method comprising the steps of:

(a) providing the apparatus of claim 1, wherein said dual-head piston comprises (1) a drive piston that fits within said bore of said drive barrel, and (2) a driven piston that fits within said bore of said gel-dispensing barrel;

(b) introducing a gel into said gel-dispensing barrel; and (c) applying pressure to said drive piston by delivering substantially incompressible fluid from said remotely positioned pump to said gel dispenser assembly, whereby said gel is caused to emerge from said gel-dispensing nozzle.

10. An apparatus for dispensing a gel into a container, said apparatus comprising:

(a) a gel dispenser assembly comprising
  (1) a gel-dispensing barrel; and
  (2) a gel-dispensing nozzle, said gel-dispensing nozzle having a tip designed so that when said tip is in contact with a target surface, at least a portion of said gel within said tip is not completely sealed within said tip by said target surface; and (b) a pump positioned remotely from said gel dispenser assembly for delivering substantially incompressible fluid to said gel dispenser assembly.

11. The apparatus of claim 10, wherein said tip is a beveled tip.

12. The apparatus of claim 10, wherein said tip of said nozzle is retractable.

13. A method for dispensing a gel into a container, said method comprising the steps of:

(a) providing the apparatus of claim 1, wherein said gel-dispensing nozzle has a tip designed so that when said tip is in contact with a target surface, at least a portion of said gel within said tip is not completely sealed within said tip by said target surface;

(b) introducing a gel into said gel-dispensing barrel; and (c) applying pressure to said gel by a substantially incompressible fluid delivered by a pump positioned remotely from said gel dispenser assembly, whereby said gel is caused to emerge from said gel-dispensing nozzle.

14. The method of claim 13, wherein said gel-dispensing nozzle is close to or in contact with a target surface when said gel emerges from said gel-dispensing nozzle.

15. A method for dispensing a gel into a container, said method comprising the steps of:

(a) providing the apparatus of claim 1, wherein said gel-dispensing nozzle has a tip designed so that when said tip is in contact with a target surface, at least a portion of said gel within said gel within said tip is not completely sealed within said tip by said target surface;

(b) introducing a gel into said gel-dispensing barrel of said apparatus;

(c) positioning said apparatus so that said tip of said gel-dispensing nozzle is in contact with a target surface;

(d) applying pressure to said gel by a substantially incompressible fluid delivered by a pump positioned remotely from said gel dispenser assembly, whereby said gel is caused to emerge from said gel-dispensing nozzle; and (e) moving said tip of said gel-dispensing nozzle along said target surface to wipe said gel from said tip of said gel-dispensing nozzle.

16. The method of claim 13, wherein the amount of gel dispensed does not exceed 1.0 $\mu$L.

17. The method of claim 15, wherein the amount of gel dispensed does not exceed 1.0 $\mu$L.

* * * * *